United States Patent [19]

Hunter et al.

[11] Patent Number: 4,561,540
[45] Date of Patent: Dec. 31, 1985

[54] MICROSCOPE DRAPE

[75] Inventors: James D. Hunter; James J. Smith, both of Jacksonville, Fla.

[73] Assignee: Xomed Inc., Jacksonville, Fla.

[21] Appl. No.: 561,384

[22] Filed: Dec. 14, 1983

[51] Int. Cl.[4] .......................... B65D 85/38; G02B 0/00
[52] U.S. Cl. ...................................... 206/305; 383/71; 350/587
[58] Field of Search ........................... 206/305; 383/71

[56] References Cited

U.S. PATENT DOCUMENTS

| | | | |
|---|---|---|---|
| 2,471,701 | 5/1949 | Post | 383/71 |
| 3,311,288 | 3/1967 | Lemelson | 383/71 |
| 3,528,720 | 9/1970 | Treace | 206/305 |
| 3,565,738 | 2/1971 | Kirkpatrick | 383/71 |
| 3,759,438 | 9/1983 | Ruda | 383/71 |

Primary Examiner—William T. Dixson, Jr.
Attorney, Agent, or Firm—Richard H. Brink

[57] ABSTRACT

A microscope drape fabricated from a very thin, transparent heat-resistant plastic film which is adapted to completely house an operating microscope including its support arms, is provided with an improved means for securing the tubular ocular housing extension of the drape to the oculars of the microscope which consists of a thin malleable strip attached to the ocular housing which permits the ocular housing to be secured to the microscope by crimping and folding over the metal strip after positioning the ocular housing on an ocular of a microscope.

7 Claims, 6 Drawing Figures

MICROSCOPE DRAPE

FIELD OF THE INVENTION

This invention relates to a sterilized, disposable drape for an operating microscope including its support arm and in particular to an improvement in the structural details of that portion of the drape which secures the drape to the oculars of the microscope.

BACKGROUND OF THE INVENTION

Microscope drapes are commonly used in surgical procedures to completely house an unsterile microscope and its support arm in a manner to substantially preclude the exhaust of heated air into an operating room at a location adjacent to the operating zone and/or the patient being operated upon. The sterile covering will also prevent the surgeon's hands from coming into contact with the non-sterile microscope.

Various means of securing the drape to the oculars of a microscope have been used. In general, the ocular housing portions of the drape are pulled downwardly over and then securely though releasably fastened to oculars as described in U.S. Pat. No. 3,698,791 by the use of pressure sensitive adhesive and very commonly by the use of rubber bands.

Pressure sensitive adhesive transfer tape with a removable top liner which covers the tape prior to application of the drape may be attached adjacent to the opening for the oculars. The liner is removed and the exposed adhesive used to effect a closure. This type of closure is frequently a one chance operation because if the closure is not adequate and insufficient adhesive is left to adjust the closure, the closure cannot be made more secure. Another problem is present with this type of means for closure. If the liner is inadvertently removed during drape installation or extreme care is not taken in handling the drape after the liner is removed, the adhesive may contact and stick to the drape body and any attempt to separate the drape body from the adhesive will likely result in a torn drape or the drape may stick to the surgical gloves of the nurse installing the drape.

As mentioned above, rubber bands may be used to effect a closure. They are commonly attached to the drape by the drape manufacturer with masking tape when the drape is packaged. To secure the drape to the oculars, the rubber bands must first be removed from the attachment point and then slipped over the oculars. This requires manual skill and is time consuming. Additionally, if a rubber band breaks or is dropped, sterile replacements are required which may not be readily available.

Interference fit ocular housings have been used; however, they require intense concentration and dexterity to install over the oculars. The aperture of the housing must be precisely sized to each particular type of ocular and torn seams frequently result from stress during installation.

It is apparent from the foregoing that none of the above-described methods of securing the ocular housings of microscope drapes to the oculars is entirely satisfactory.

SUMMARY OF THE INVENTION

Accordingly, it is the object of the present invention to overcome the above-defined problems with the application of sterile drapes to microscopes in operating rooms.

It has been found by this invention that such problems may be overcome by providing a drape for operative microscopes comprising generally the following:

A microscope drape is provided for positioning over an operating microscope in enclosing relationship thereto of generally flexible, drapable, sterilizable material; said drape comprising an elongate, continuous, substantially tubular drape open at one end and terminating at the other end in at least one elongate, outward projecting cylinder defining ocular housing for receiving the ocular of the microscope. An elongate strip of thin malleable metal is attached to the ocular housing to provide means for releasably securing the ocular housing to an ocular of the microscope.

The drape of this invention solves the problem of the prior art by providing means for easily securing the drape's ocular housings to the oculars of the microscope. Gathering of the loose material around the oculars and bending and crimping the strip of thin malleable metal forms a substantially airtight seal around the oculars of the microscope.

Accordingly, this invention has provided an improved microscope drape which overcomes problems presented with prior microscope drapes for covering an unsterile operating microscope.

BRIEF DESCRIPTION OF THE DRAWINGS

Some of the objects and advantages of the invention having been stated; other objects and advantages will appear when taken in conjunction with the accompanying drawings, in which.

DESCRIPTION OF ILLUSTRATED EMBODIMENT

Figure 2:
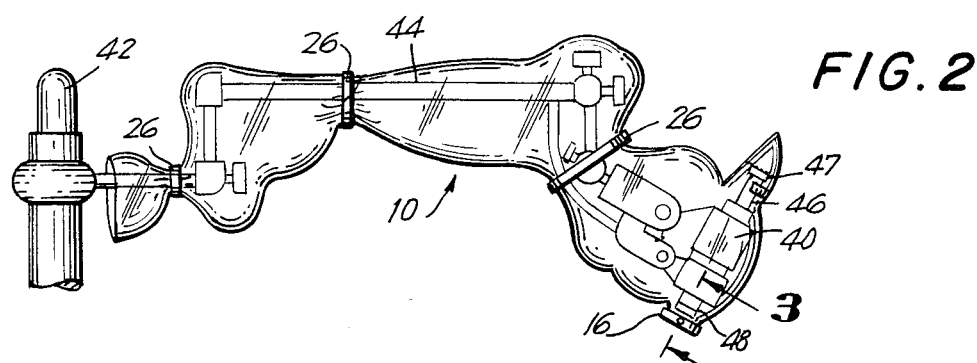
FIG. 2 is a side view of a typical arm-supported operating mircroscope having the drape associated therewith.
Figure 3:
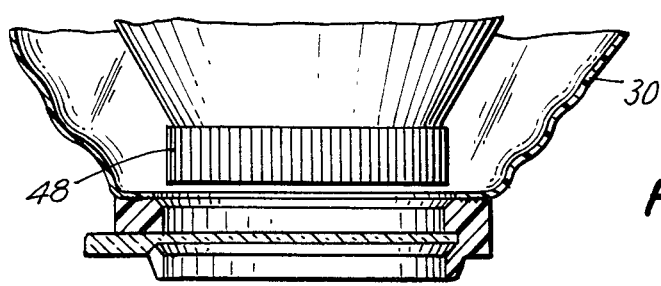
FIG. 3 is a view partly in section along line 3—3 of FIG. 2 illustrating the relationship of the drape lens, or lens housing with the objective lens ring of the type which projects from the lens housing of a microscope.

Referring now to FIG. 2 of the drawings, there is illustrated therein a generally conventional microscope generally indicated by the reference numeral 40, which is adjustably mounted relative to an upright 42 or other member by means of a support arm 44. The microscope includes oculars 46 and objective lens 48 and an illuminating lamp not illustrated. Each ocular 46 has an ocular eye-piece 47 which is adjustable to enable the user to adjust it to the desired position for viewing various portions of a patient upon which surgery is to be performed and during such surgery.

Figure 1:
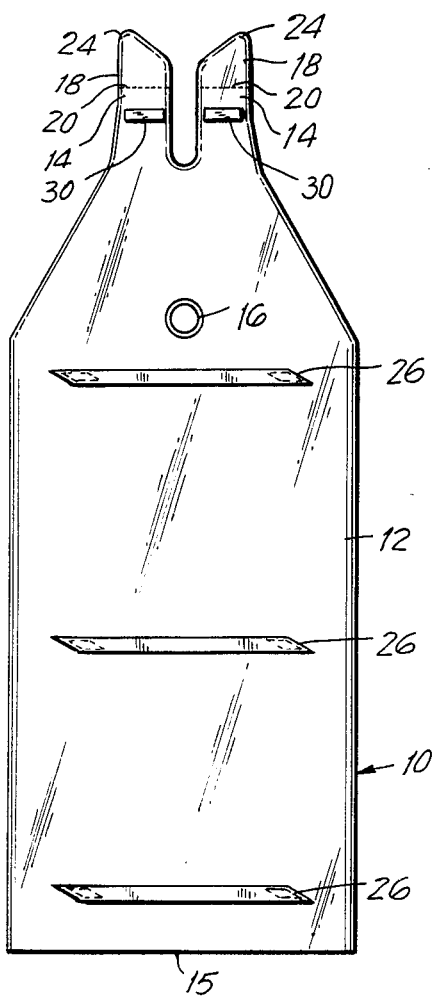
FIG. 1 is a plan view showing the disposable, sterile drape of the present invention.

With further reference to the drawings, the numeral 10 denotes generally an elongate drape fabricated from a thin, preferably transparent, soft inexpensive flexible, sterilizable nonglare polyethylene or polypropylene or other polymer or co-polymer film approximately 2 millimeters thick. The drape comprises a substantially tubular main body portion 12 best illustrated in FIG. 1, which is open at one end 15 and wherein the other end terminates in one or more cylindrical extensions or ocular housings 14 dimensioned to telescopically engage the oculars 46 of a microscope. The numeral 16 denotes objective lens cover which contains a lens of transparent material which covers the objective lens of the microscope.

Each ocular housing 14 has a closed end 18 and a row of perforations 20 which completely circumscribe the housing. The closed ended portion of the ocular housing is preferably of a tapered shape with the apex 24 of the taper to one side to facilitate removal of the closed ended portion from the remainder of the ocular housing to expose the ocular lens or eyepiece. The ocular housings contain a thin strip of malleable metal 30 which is attached to the ocular housing below the perforations 20 preferably about 1 inch below the perforations and of sufficient length to tighten the housing around the ocular when the strip is crimped or squeezed together. The strip can be of aluminum, copper, lead and the like but preferably aluminum. The thickness of the strip is 3/1000 to 8/1000 inches and preferably 5/1000 inches and has a width of ¼ to 1 inch and preferably ½ inch. Basically the material of the strip must have the property of being bendable with little force and of maintaining a crease when bent to counteract the tendency of the drape to spring back. The strip releasably secures the housing to the oculars. The malleable metal strip can be attached to the drape material by any convenient means, such as by adhesive as shown in the preferred embodiment and denoted by the numeral 32.

Figure 4:
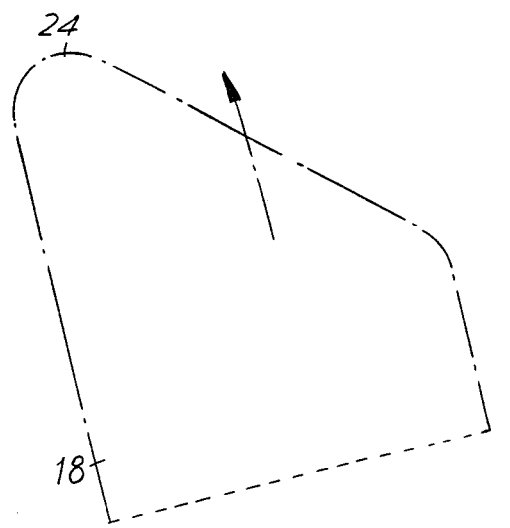
FIG. 4 illustrates the manner in which the ocular drape housings are secured to and in locking relationship on the oculars and the manner in which the ends of the ocular housings are removed for providing the desired relationship between the ocular housing and the oculars.
Figure 4:
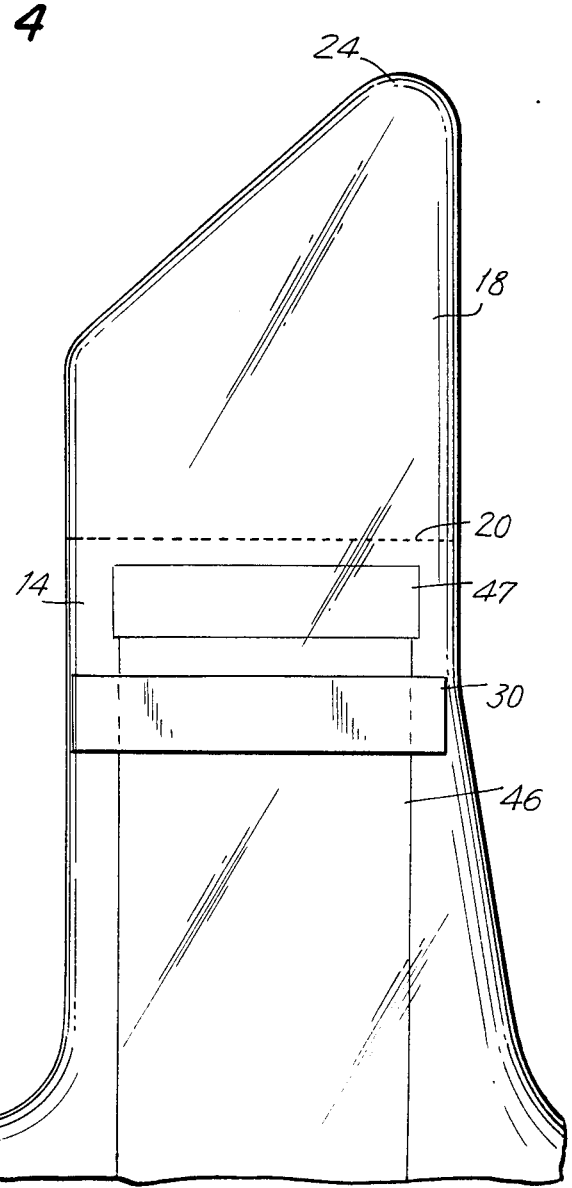
Figure 5:
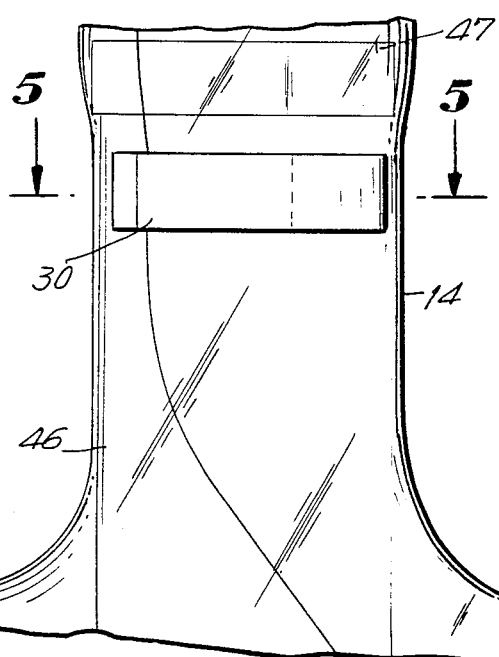
FIG. 5 is a sectional view taken generally along line 5—5 of FIG. 4.
Figure 5:
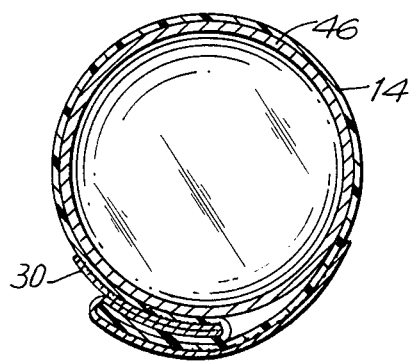
Figure 6:
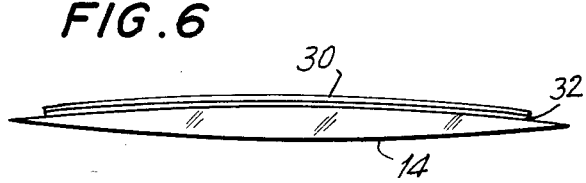
FIG. 6 is a top view of the ocular housing portion of the drape with the top portion of the housing removed but not mounted on a microscope.

In use, the body of the microscope drape is pulled over the microscope and the ocular housings pulled over the oculars. The operating room nurse merely pinches the strip on each ocular housing and folds the pinched section down upon itself as illustrated in FIG. 5. The closed ended portion of each ocular housing is pulled at the apex and separated at the perforations as shown in FIG. 4. In this manner the ocular housing engages each ocular with sufficient tightness to maintain the sterile drape over the oculars but exposing the ocular lens or eyepiece and substantially reduces the escape of air from the interior of the drape via the housing and exposes only the ocular lens of the microscope. Straps 26 with adhesive are provided to fashion the drape around the microscope.

Thus according to this invention an improved microscope drape has been provided for covering a microscope during surgical procedures which overcomes the above-defined problems with prior microscope drapes.

While this drape has been described and exemplified in terms of the preferred embodiment, those skilled in the art will appreciate that modifications can be made without departing from the spirit and scope of this invention.

What is claimed is:

1. A disposable microscope drape for positioning over an operating microscope in enclosing relationship thereto comprising an elongate, continuous, substantially tubular drape open at one end and terminating at the other end in at least one elongate, outwardly projecting cylinder-defining ocular housing for receiving an ocular of the microscope, said ocular housing having attached thereto an elongate strip of malleable metal having a length substantially less than that required to encircle said ocular housing whereby loose material may be gathered tightly and secured around the ocular of said microscope by manually folding and creasing the metal strip upon itself.

2. The microscope drape of claim 1 wherein the malleable metal strip is aluminum.

3. The microscope drape of claim 2 wherein the strip of malleable metal has a thickness from about 3/1000 inches to 8/1000 inches.

4. The microscope drape of claim 2 wherein the strip of malleable metal has a thickness of about 5/1000 inches.

5. The microscope drape of claim 2 wherein the strip of malleable metal has a width of about ¼ to 1 inch.

6. The microscope drape of claim 2 wherein the strip of malleable metal has a thickness of 5/1000 inches and a width of ½ inch.

7. The microscope drape of claim 1 wherein the end of the ocular housing terminates in a tapered shape.

* * * * *